United States Patent [19]

Schally et al.

[11] 4,328,134

[45] May 4, 1982

[54] ANOREXIGENIC PEPTIDES

[76] Inventors: Andrew V. Schally, 5025 Kawanee Ave., Metairie, La. 70002; David H. Coy, 4319 Perrier St., New Orleans, La. 70115

[21] Appl. No.: 147,112

[22] Filed: May 6, 1980

[51] Int. Cl.$^3$ .................... C08L 37/00; C07C 103/52
[52] U.S. Cl. ....................... 525/54.11; 260/112.5 TR
[58] Field of Search .............. 424/177; 260/112.5 TR; 260/8

[56] References Cited

U.S. PATENT DOCUMENTS

| | | | |
|---|---|---|---|
| 3,749,706 | 7/1973 | Geiger et al. | 260/112.5 TR |
| 3,876,624 | 4/1975 | McGregor | 260/112.5 TR |
| 3,912,705 | 10/1975 | Fujino et al. | 260/112.5 TR |
| 3,959,248 | 5/1976 | Veber et al. | 260/112.5 TR |
| 4,066,635 | 1/1978 | Gillessen et al. | 424/177 |

OTHER PUBLICATIONS

Hofmann et al., *Journal of Med. Chem.* 1970, 13, 1099–1101.

Chang, et al., *Journal of Med. Chem.* 14, 1971, 484–487.

*Primary Examiner*—Delbert K. Phillips
*Attorney, Agent, or Firm*—Eyre, Mann, Lucas & Just

[57] ABSTRACT

There are disclosed peptides of the formula A-B-C and pharmaceutically acceptable salts thereof, in which A is selected from the group consisting of L-pyroglutamyl, D-pyroglutamyl, and L-homo-pyroglutamyl; B is selected from the group consisting of L-histidyl, L-3'-methylhistidyl, D-histidyl, L-phenylalanyl, L-p-aminophenylalanyl, and L-$\beta$-(pyrazolyl-1)alanyl; and C is selected from the group consisting of glycine and lower alkyl esters thereof, glycinamide and lower alkyl amides thereof, 2-amino-1-hydroxyethyl, D-alanine, L-$\beta$-(2-thienyl)-alanine, and NHR$^1$ in which R$^1$ is lower alkyl, with the proviso that C may not be glycine or glycinamide when A is L-pyroglutamyl and B is L-histidyl.

The compounds have anorexigenic properties, inhibit excessive gastric and pancreatic secretion, and cause activation in the CNS. Methods for their preparation and use are also disclosed.

6 Claims, No Drawings

ANOREXIGENIC PEPTIDES

BACKGROUND OF THE DISCLOSURE (a) Field of Invention

This invention relates to peptides of the formula A-B-C (1) and pharmaceutically acceptable salts thereof in which A is selected from the group consisting of L-pyroglutamyl (L-H-(pyro)-Glu), D-pyroglutamyl (D-H-(pyro)-Glu), and L-homo-pyroglutamyl (L-H-homo-(pyro)-Glu); B is selected from the group consisting of L-histidyl (L-His), D-histidyl (D-His), L-3'-methylhistidyl (L-N$^{im}$-3-MeHis), L-phenylalanyl (L-Phe), L-p-aminophenylalanyl(L-p-NH$_2$Phe), and L-$\beta$-(pyrazolyl-1)alanyl (L-$\beta$-(pyrazolyl-1)Ala); and C is selected from the group consisting of glycine and lower alkyl esters thereof (Gly-OR in which R is H or lower alkyl), glycine amide and lower alkyl amides thereof (Gly-NHR in which R is H or lower alkyl), 2-amino-1-hydroxyethyl (GLy-ol), D-alanine (D-Ala), L-$\beta$-(2-thienyl)alanine, and NHR$^1$ in which R$^1$ is lower alkyl, with the proviso that C may not be glycine or glycinamide when A is L-pyroglutamyl and B is L-histidyl. This invention also relates to a process for preparing said compounds of formula 1, to intermediates used in said process, and to the use of said compounds in mammals as anorexigenic agents in methods of treatment of obesity and of other pathological conditions in which a reduction of food intake is indicated, as well as to their use in methods of treatment of pathological states associated with excessive secretion of gastric acid or of pancreatic fluid such as gastric or duodenal ulcers or acute pancreatitis, and in certain critical states of the central nervous system such as reduced consciousness or coma due to brain injury.

The abbreviations used throughout this application for the amino acids or the residues thereof as well as for the protective groups are generally based on recommendations of the IUPAC-IUB Commission on Biochemical Nomenclature, see Biochemistry 11, 1726 (1972), for example: (pyro)-Glu, 5-oxoproline or pyroglutamic acid; homo-(pyro)-Glu, homopyroglutamic acid; His, histidine; N$^{im}$-3-MeHis, 3'-methylhistidine; Phe, phenylalanine; p-NH$_2$ Phe, p-aminophenylalanine, $\beta$-(pyrazolyl-1)Ala, $\beta$-(pyrazol-1-yl)-alanine; Gly, gly-cine, Gly-ol, 2-aminoethanol; and Thi, $\beta$-(2-thienyl) alanine. All amino acids have the natural or L-configuration unless stated otherwise; D-His is the residue of D-histidine, D-(pyro)-Glu is the residue of D-pyroglutamic acid, and D-Ala is the residue of D-alanine. The abbreviations Me and Et are used for methyl and ethyl, respectively. The abbreviations used for the protective groups are, for example: Boc, t-butyloxycarbonyl; Z, benzyloxycarbonyl; Tos, tosyl; Dnp, dinitrophenyl; N$^{im}$ means the imidazole nitrogen of histidine; and Y is a suitable anchoring group used in solid phase synthesis linked to a solid resin support, preferably

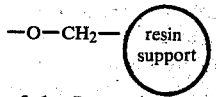

(b) Background of the Invention The humoral control of appetite, especially via the hypothalamus, has been under discussion for many years, see e.g. the review by Schally et al., Am. J. Med. Sci. 248, (1), 79 (1964) and references cited therein. It was known at that time that the hypothalamus was involved in the regulation of food intake. Electrical stimulation of the lateral hypothalamic area produces hyperphagia and its destruction leads to aphagia. Contrarywise, the stimulation of the ventromedial nucleus decreased food intake, and its destruction leads to hyperphagia and obesity.

The obesity syndrome which follows the administration of gold thioglucose is in part the result of hyperphagia associated with hypothalamic lesions produced by this agent. Theories on the neural control of hunger, appetite and satiety have been ably reviewed by others and several mechanism have been suggested: (1) Thermostatic theory. According to this theory, specific dynamic action of food and its effect on body temperature regulate appetite. (2) Chemostatic theories. These postulate that appetite is regulated by intracellular or extracellular levels of glucose (glucostatic theory), lipids, (lipostatic theory, and also by the concentration of certain metabolites such as serum amino acids. (3) Another group of theories assert that sensations from the digestive tract associated with eating and presence of food in the stomach and the intestine regulate appetite. Among factors involved in the production of satiety or cessation of eating is the distention of stomach by food or non-nutritious substances. Gastric contractions may be related to hunger behavior, but these contractions are the same in animals rendered aphagic or hyperphagic by hypothalamic injury as in normal animals deprived of food and water.

These theories do not explain all the experimental facts, among them that the diabetic animal can be hungry. Schally et al. cited above then suggest that the obesity seen in animals with hypothalamic lesions could be mediated by a humoral rather than a neurogenic mechanism and that the hypothalamus may elaborate a substance involved in a central control of appetite. Preliminary evidence is cited which suggests the presence in neurohypophyseal extract of a substance which will affect the dynamic phase of weight gain in gold thioglucose-treated mice.

A more recent brief review of the status of investigation concerning hypothalamic control of food intake and obesity is found in Schally et al. Recent Progress in Hormone Research, Proceedings of the 1967 Laurentian Hormone Conference, 24, 497 (1968), in particular pp. 570–571 and references cited therein. Among those references is the paper by Schally et al, in Science 157, 210 (1967) which showed that administration of enterogastrone purified from hog duodenum reduced the food intake of mice fasted for 17 hours. This effect was greatest during the first 30 minutes, but the cumulative reduction continued for at least 4 hours. Other peptides prepared from hog duodenum or colon, as well as glucagon, secretin, glucose, and bovine serum albumin were ineffective. The authors state that this effect could have been due to a direct elimination of gastric hunger contractions or could have been mediated by an action through the central nervous system involving release of hypothalamic substances, although positive evidence for any hypothalamic neurohumors responsible for the indirect or direct control of appetite was still lacking at that time.

It would appear that this positive evidence was supplied by Tyrgstad et al., Acta Endocrinologica 89, 196 (1978) who isolated a number of peptides which produced metabolic behavioural effects from the urine of patients suffering from the hypothalamic syndrome congenital, general lipodistrophy. Anorexia nervosa is associated with hypothalamic disturbances. In primary hypothalamic anorexia nervosa, the hypothalamic-pituitary axis is disturbed, resulting in low release of gonadotropins, amenorrhea, loss of diurnal rhythm for ACTH secretion, reduced secretion of thyrotropin, and initial increase and later decrease in secretion of somatotropin.

Precipitates from urine specimens from 25 patients diagnosed as anorexia nervosa were chromatographed on Sephadex G-25 gel columns, and could be divided into four different patterns: One was similar to that for normal controls, one similar to that observed for patients with schizophrenia, 5 patients with a hysteriform type of neurosis had a third form of pattern, and 10 girls considered to have a primary "hypothalamic" type of anorexia nervosa also had typical chromatograms. Fractions influencing appetite in mice were found in the latter group only. Two peptides influencing appetite were purified through several steps of chromatography. One increased appetite and one depressed it in mice into which the peptides were injected. The peptides are enveloped in peptide-carrier proteins and are thus protected against enzymatic degradation, which made their isolation from urine possible.

The structure of the anorexigenic peptide was elucidated by Reichelt et al., Neuroscience 3, 1207 (1978) who worked in close association with Trygstad cited above, and it was determined to be the tripeptide H-(pyro)-Glu-His-GlyOH; this was confirmed by synthesis.

A dose of 12 nmole of appetite-retarding peptide injected in mice daily for 20 days reduced food consumption from 5.7 to 3.0 g per day for about 6 months. Body weight dropped from a mean of 35 g to a minimum of 24 g.

The tripeptide had no acute effect on blood glucose or serum insulin levels and seemed to act on receptors localized in the hypothalamic centers controlling appetite.

The appetite-stimulating peptide increased daily consumption of food to more than 10 g, and mean body weight jumped to 57 g. The structure of the appetite-stimulating peptide could not be identified.

Two similar factors inducing increased and decreased feeding behavior were also isolated from patients with genetic metabolic obesity.

We have found that peptides of the formula (1) A-B-C in which A, B, and C are as defined above are more active and have a longer duration of activity in reducing appetite and inhibiting food intake than the tripeptide pryoglutamyl-histidyl-glycine (H-(pyro)-Glu-His-Gly-OH) isolated from urine by Trygstad et al., and by Reichelt et al., both cited above. Those peptides of formula (1) and their pharmaceutically acceptable salts which are biologically equivalent to the above peptides themselves, are therefore useful as anorexiant agents in the treatment of obesity and of associated pathological conditions which require a reduction in food intake. They also reduce gastric and pancreatic secretion and are thus useful in the treatment of pathological conditions associated with excessive production of gastric acid and/or of pancreatic fluid. Moreover, they exert certain activities upon the central nervous system which makes them useful in the acute treatment of states of reduced consciousness.

They possess the advantages over the natural tripeptide of being more active and of having a longer duration of activity and both those attributes are of practical significance: the lesser minimum effective doses reducing side effects as well as the cost for the preparation of the compounds and the longer acting properties reducing the need for frequent administration.

In view of the biological equivalence of the peptides of formual 1 and of their pharmaceutically acceptable salts, all preceding and subsequent references to the peptides of formula 1 are to be understood as covering both said peptides and said salts.

SUMMARY OF THE INVENTION

The compounds of this invention are selected from the group consisting of compounds of formula (1) A-B-C in which A, B, and C are as defined above and pharmaceutically acceptable salts thereof, as well as the protected intermediates linked to a solid resin support used in the preparation of the above compounds of formula (1).

The protective groups used in the stepwise solid phase syntheses of the intermediates are selected from those which are capable of being removed by one or more chemical treatments without affecting the desired compound of formula (1). Moreover, said protective groups are also selected so as to be capable of being removed in a single step together with other protective groups, for example, together with the anchoring group Y as defined above. A particularly suitable protective group for the terminal amino group of any amino acid which is used in the stepwise or solid phase synthesis of the above intermediates is $R^2$, t-butyloxycarbonyl (Boc); suitable protective groups for the imidazole nitrogen of histidine are $R^3$, preferably tosyl (Tos) or dinitrophenyl (Dnp); a suitable protective group for the phenylamino group in p-aminophenylalanine is $R^4$, benzyloxycarbonyl (Z); and a suitable anchoring group for attachment to the resin support is the group Y as defined above, e.g. —O—$CH_2$—. The above protective groups are stable to the reagents and under the reaction conditions used to remove the protective group on the terminal amino group and in the subsequent coupling reaction.

The term "lower alkyl" designates straight or branched alkyl groups having from 1–3 carbon atoms.

The peptides of formula 1 are prepared by stepwise solid phase synthesis starting at the carboxy terminal end. Briefly, the particular amino acid selected to represent C, or B when C is $NHR^1$ wherein $R^1$ is lower alkyl, having a suitably protected α-amino group and other protective groups attached thereto if required, and anchored to the resin support by means of the group Y defined above, is deprotected on the α-amino group and coupled with the particular amino acid chosen to represent B, or A when C is $NHR^1$ as defined above, using a suitable dialkyl or dicycloalkyl carbodiimide as the coupling reagent. The above procedure is repeated until the desired number of amino acids have been coupled together. The terminal amino group is then deprotected, other protective groups, if present, as well as the anchoring group Y are also removed, and the desired crude peptide is obtained by removal of the solvent. The crude product is purified by chromatography, e.g. by gel filtration, to obtain the desired peptide in the pure state.

DETAILS OF THE INVENTION

The starting materials for the peptides of formula 1 are either commercially available or they may be conveniently prepared by procedures which are known per se. Thus, all amino acids used in the synthesis of the above peptides are commercially available except as follows: homo-(pyro)-glutamic acid is prepared as described by Greenstein and Winitz in "Chemistry of the Amino Acids", pp. 2407–2462, J. Wiley, New York, 1961; and β-(2-thienyl)alanine is prepared as described ibid. p. 2707.

Suitable solid resin supports are chloromethylated or hydroxymethyl resins, the former being preferred. The preparation of a hydroxymethyl resin is described by M. Bodansky and J. T. Sheehan, Chem. Ind. (London) 38, 1597 (1966). A chloromethylated resin is commercially available from Bio Rad Laboratories, Richmond, Calif. In using the chloromethylated resin an ester anchoring group is formed with the α-amino protected amino acid C (or B if C is $NHR^1$ as defined above) having additional protective groups if required, as follows.

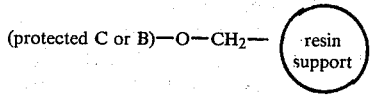

(protected C or B)—O—CH₂— resin support

A convenient procedure for converting the linked protected peptide to the C-terminal (lower alkyl) amide is to cleave the protected peptide off the resin by treatment with a lower alkylamine, cf, D. H. Coy, et al., Biochem. Biophys. Res. Commun., 57, 335 (1974), to obtain the corresponding protected peptide (lower alkyl)amide. Thereafter, the protective groups of the resulting peptide (lower alkyl)amide are removed by treatment with sodium and liquid ammonia or preferably by hydrogen fluoride cleavage to give the corresponding peptide of this invention. An alternative procedure is to cleave by transesterification with a lower alkanol, preferably methanol or ethanol, in the presence of triethylamine to obtain the corresponding ester. Said ester may be converted into the corresponding (lower alkyl)amide and subsequently deprotected as described above. When it is desired to obtain the free carboxylic acid the cleavage is preferably carried out with hydrogen fluoride in anisole, and when it is desired to obtain the acid amide the cleavage is carried out with ammonia. See also J. M. Stewart and J. D. Young, "Solid Phase Peptide Synthesis", W. H. Freeman & Co., San Fransico, 1969, pp. 40–49.

More specifically, in an embodiment of the present invention α-amino protected glycine, preferably t-butyloxycarbonylglycine, is coupled to a chloromethylated resin with the aid of a catalyst, preferably cesium bicarbonate or triethylamine. Following the coupling of the α-amino protected glycine to the resin support, the α-amino protecting group is removed, for example by using trifluoroacetic acid in methylene chloride, trifluoroacetic acid alone or hydrochloric acid in dioxane. The deprotection is carried out at a temperature between about 0° C. and room temperature. Other standard cleaving reagents and conditions for removal of specific α-amino protecting groups may be used as described by E. Schroder and K. Lubke, "The Peptides", Vol. 1, Academic Press, New York, 1965, pp. 72–75. After removal of the α-amino protecting group, the remaining α-amino protected amino acids are coupled stepwise in the desired order to obtain the desired peptide. Each protected amino acid is introduced into the solid phase reactor in about a three-fold excess and the coupling is carried out in a medium of methylene chloride or mixtures of dimethylformamide in methylene chloride. In cases where incomplete coupling has occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser, et al., Analyt. Biochem. 34, 595 (1970).

After the desired amino acid sequence has been synthesized, the protected peptide is removed from the resin support by treatment with a (lower alkyl)amine to give the corresponding protected peptide (lower alkyl)amide, and in the case where dinitrophenyl or tosyl has been used as the protecting group for the histidyl residue, the dinitrophenyl or tosyl protecting group is also removed during the treatment with the (lower alkyl)amine. The peptide may also be separated from the resin by transesterification with a lower alkanol, preferably methanol or ethanol in the presence of triethylemine, after which the recovered ester is purified by chromatography on silica gel. The collected fraction may be subjected to treatment with a (lower alkyl)amine to convert the lower alkyl ester, preferably the methyl or ethyl ester, to the carboxy-terminal (lower alkyl) amide; note that the dinitrophenyl or tosyl group, if present on the histidyl residue, will also be cleaved. The remaining side chain protecting groups of the protected alkylamide are then cleaved by procedures described above, for example by treatment with sodium in liquid ammonia or by hydrogen fluoride. Removal of the protected peptide from the resin support may also be carried out with ammonia to give the corresponding amide, or with hydrogen fluoride and anisole to give the corresponding free acid. Peptides of formula 1 wherein C is 2-aminohydroxyethyl (Gly-ol) are prepared by cleavage of an A-B dipeptide resin with 2-aminoethanol; note that dinitrophenyl or tosyl groups, if present on the histidyl residue, will also be removed by this procedure.

The peptides of formula 1 of this invention can be obtained in the form of acid addition salts. Examples of salts are those with organic acids, e.g. acetic, lactic, succinic, benzoic, salicyclic, methanesulfonic or toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid. If desired, a particular acid addition salt is converted into another acid addition salt, e.g. a salt with a non-toxic, pharmaceutically acceptable salt, by treatment with the appropriate ion exchange resin in the manner described by R. A. Boissonnas, et al., Helv. Chim. Acta, 43, 1349 (1960). Suitable ion exchange resins are cellulose based cation exchangers, for example carboxymethyl-cellulose or chemically modified, cross linked dextran cation exchangers, for example, those of the Sephadex C-type, and strongly basic anion exchange resins, for example those listed by J. P. Greenstein and M. Winitz in "Chemistry of the Amino Acids", John Wiley and Sons, Inc., New York and London, 1961, Vol. 2, p. 1456.

The peptides of formula 1 and their salts possess valuable, long-acting anorexiant, gastric and pancreatic secretion inhibiting, and CNS activating properties.

The appetite reducing and anorexigenic properties of the peptides of formula 1 are determined in feeding experiments in mice, rats, or dogs similar to those described by Trygstad et al, and by Reichelt et al., both cited above. The gastric and/or pancreatic secretion inhibiting properties of the peptides of formula 1 are determined in conscious rats, or preferably in conscious dogs, provided with esophageal, gastric, and pancreatic fistulae, and also in dogs with Heidenhain pouches, see e.g. B. P. Babkin, "Secretion Mechanism of Digestive Glands", 2nd ed., P. B. Hoeber, New York, 1950, as cited in "Physiology", E. Selkurt, editor, Little, Brown and Company, Boston, 1963, pp. 542–544; L. Olbe, Gastroenterology 32: 460, (1959); Antin et al., Journal of Comparative and Physiological Psychology 89: 784 (1975); and Liebling et al., ibid. 89: 955 (1975). The activities of the peptides of formula 1 upon the central nervous system, in particular their characteristic spectrum of neurotropic effects can be determined by a variety of CNS tests described e.g. by A. J. Kastin, R. D. Olson, A. V. Schally and D. H. Coy, Life Sciences 25: 401 (5) (1975); A. J. Prange, G. R. Breese, J. M. Cott, B. R. Martin, B. R. Cooper, I. C. Wilson, and N. P. Plotnikoff, Life Sciences 14: 447 (1974), and M. Brown and W. Vale, Endocrinology 96: 1333 (1975).

The mouse, rat, or dog is the preferred experimental animal for determining the appetite reducing or anorexigenic properties of drugs, as well as for determining their gastric and/or pancreatic secretion inhibiting properties, and excellent parallelism between animal studies and clinical results observed in humans has been demonstrated in numerous cases, for example in humans under controlled ingestion of liquid diet orally or intragastrically see e.g. H. A. Jordan, Journal of Comparative and Physiological Psychology 68. 498 (1969); G. A. Bray and F. L. Greenway, Clinics in Endocrinology and Metabolism 5 (2), 455 (1976), and H. D. Janowitz, "Role of gastrointestinal tract in regulation of food intake". as cited in "Handbook of Physiology", Section 6, Alimentary Canal. C. F. Code and W. Heidel, Editors, American Physiological Society, Washington, 1967.

The effectiveness of the peptides of formula 1 and of their pharmaceutically acceptable salts in reducing appetite and as anorexigenic agents may be demonstrated by the use of rats. The rat is one of the preferred experimental animals for demonstrating the activity of drugs which inhibit food intake, and parallelism between resultss obtained in rats and in humans has been established by many different authors. For example, G. A. Bray in "The Obsese Patient", Vol IX of "Major Problems in Internal Medicine", by W. B. Saunders Company, Philadelphia—London—Toronto, 1976, has in chapter 9 entitled "Drug Therapy for the Obese Patient" the section "Pharmacology—Effects on the Central Nervous System"; on p. 364 Table 9-4 shows data obtained in rats demonstrating, inter alia, the reduction in food intake caused by a number of anorexigenic drugs; and the section "Clinical Use of Anorectic Drugs" shows in Table 9-7 on p. 369, all the same drugs as in Table 9-4 cited above as being clinically useful.

The above properties make the peptides of formula 1 useful for administration to mammals in veterinary practice as well as in human medicine.

The appetite-reducing and anorexigenic properties are useful in the treatment of obesity, including the pre-operative reduction in body weight which is frequently required in obese patients prior to major surgery. Those properties are also useful in the treatment of other pathological conditions which require a reduction in food intake and body weight, for example in certain forms of diabetes or of circulatory diseases.

The properties of the peptides of formula 1 to reduce secretion of gastric acid and of pancreatic fluid are useful in the treatment of pathological conditions associated with gastric and/or pancreatic hypersecretion of gastric acid or of gastrin, pepsin, or histamine, such as gastric or duodenal ulcers, or acute pancreatitis.

The effects of the peptides of formula 1 upon the central nervous system show a neurotropic profile of activities which is significantly different from the profiles exhibited by the tricyclic antidepressants and by conventional drugs. The CNS activation caused by the peptides of formula 1 makes them useful in the treatment of states of reduced consciousness or coma due to brain injury, for example in cases of cerebral trauma or tumours, in cases of severe freezing or in certain postoperative conditions, as well as in states of reduced consciousness caused by certain vascular diseases or by excessive intake of drugs such as in drug intoxications.

When one of the peptides of formula 1 or a pharmaceutically acceptable salt thereof is employed in mammals as an agent for reducing appetite for food or as an anorexigenic agent in the treatment of obesity and of other pathological conditions which require a reduction in food intake, or as an agent to inhibit excessive gastric or pancreatic secretion, or as a CNS activation agent, e.g. in mice, rats, or dogs, it may be used alone or in combination with pharmaceutically acceptable carriers, the proportion of which is determined by the solubility and chemical nature of the compound, chosen route of administration and standard biological practice. For example, an amount of the compound effective to reduce appetite and/or food intake may be administered orally in solid form containing such excipients as starch, sugar, certain types of clay and the like.

Similarly, such an amount may also be administered orally in the form of solutions or suspensions, or the compound may be injected parenterally. For oral or parenteral administration the compound may be used in the form of a sterile solution or suspension in a pharmaceutically acceptable liquid carrier such as water, ethanol, propylene glycol, or polyethylene glycol, containing other solutes or suspending agents, for example enough saline or glucose to make the solution isotonic, bile salts, acacia, gelatin, sorbitan monoleate, polysorbate 80 (oleate esters of sorbitol and its anhydrides copolymerized with ethylene oxide), i.e. "Tween 80" (registered Trademark) and the like.

The dosage of the present peptides of formula 1 will vary with the form of administration and with the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results in reducing appetite and/or food intake, in inhibition of gastric and/or pancreatic secretion, or in activation of the central nervous system without causing any harmful or deleterious side effects and preferably at a level that is in a range of from about 1.0 mcg to about 250 mcg per kg body weight per day, although as aforementioned, variations will occur. However, a dosage level that is in the range of from about 5 mcg to about 100 mcg per kg per day, preferably in divided doses, is most desirably employed in order to achieve effective results.

The appetite and/or food intake reducing activities as well as the gastric and/or pancreatic secretion inhibiting properties and the activities upon the central nervous system of the peptides of formula 1 are weight for weight much higher than those of a number of well known drugs commonly used for the same purposes. Moreover, most of the clinically useful anorexiants have structures which are related to phenethylamine and show a number of undesirable side effects associated with that latter structure. The peptides of formula 1 are not related to phenethylamine and have the advantage of not exhibiting the undesirable side effects known to be associated with that latter structure. Furthermore, they are of low orders of toxicity and are thus safe for administration.

When a peptide of formula 1, preferably in the form of an acid addition salt thereof, is employed in human medicine, it may be administered systemically, ether by intravenous, subcutaneous, or intramuscular injection, or by sublingual or nasal administration, in compositions in conjunction with a pharmaceutically acceptable vehicle or carrier.

Pharmaceutical compositions of the compounds of formula 1 may be also formulated so as to be suitable for oral administration. For such purposes the active ingredient can be mixed with suitable known pharmaceutical excipients and incorporated by known means into such formulations as tablets, capsules, suspensions, emulsions, solutions or dispersible powders.

Solid formulations may be filled into capsules for oral administration. Such formulations suitable for filling into capsules may contain the solid active ingredient in admixture with solid materials which have a buffering action for example colloidal aluminium hydroxide or calcium hydrogen phosphate, or with an inert solid such as lactose.

Formulations of the compositions of the compounds of formula 1 as tablets which may be coated and either effervescent or non-effervescent may be carried out according to the known art. Inert diluents or carriers for example magnesium carbonate or lactose are used together with conventional disintegrating agents for example maize starch and alginic acid and lubricating agents for example magnesium stearate.

For administration by the nasal route as drops or spray it is preferred to use the peptides of formula 1 in solution in a sterile aqueous vehicle which may also contain other solutes such as buffers or preservatives, as well as sufficient quantities of pharmaceutically acceptable salts or of glucose to make the solution isotonic. Doses by the intranasal route range from 1.0 to 250 mcg/kg/day or preferably about 5 to about 100 mcg/kg/day.

The peptides of formula 1 may also be administered as nasal powders or insufflations. For such purposes the peptide of formula 1 is administered in finely divided solid form together with a pharmaceutically acceptable solid carrier, for example a finely divided polyethylene glycol ("Carbowax 1540"), finely divided lactose, or very finely divided silica ("Cab-O-Sil"). Such compositions may also contain other excipients in finely divided solid form such as preservatives, buffers, or surface active agents.

The peptides of formula 1 may also be administered in one of the long-acting, slow-release or depot dosage forms described below, preferably by intramuscular injection or by implantation. Such dosage forms are designed to release from about 5 mcg to about 100 mcg per kilogram body weight per day.

It is often desirable to administer the peptides of formula 1 continuously over prolonged periods of time in long-acting, slow-release, or depot dosage forms. Such dosage forms may either contain a pharmaceutically acceptable salt of the compound having a low degree of solubility in body fluids, for example salts with pamoic or tannic acid or carboxymethylcellulose, or they may contain the peptide of formula 1 in the form of a water-soluble salt together with a protective carrier which prevents rapid release. In the latter case, for example, the peptide of formula 1 may be formulated with a non-antigenic partially hydrolyzed gelatin in the form of a viscous liquid; or it may be absorbed on a pharmaceutically acceptable solid carrier, for example zinc hydroxide with or without protamine, and may be administered in suspension in a pharmaceutically acceptable liquid vehicle; or the peptides of formula 1 may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, Mack Publishing Co., Easton, Pa., 1975. Long-acting, slow-release preparations of the peptides of formula 1 may also be obtained by microencapsulation in a pharmaceutically acceptable coating material, for example gelatine, polyvinyl alcohol or ethyl cellulose. Further examples of coating materials and of the processes used for microencapsulation are described by J. A. Herbig in "Encyclopedia of Chemical Technology", Vol. 13, 2nd Ed., Wiley, New York, 1967, pp. 436–456. Such formulations, as well as suspensions of salts of the peptides of formula 1 which are only sparingly soluble in body fluids, are designed to release from about 5 mcg to about 100 mcg of the peptide per kilogram body weight per day, and are preferably administered by intramuscular injection. Alternatively, some of the solid dosage forms listed above, for example certain sparingly water-soluble salts or dispersions in or adsorbates on solid carriers of salts of the peptides of formula 1, for example dispersions in a neutral hydrogel of a polymer of ethylene glycol methacrylate or similar monomers cross-linked as described in U.S. Pat. No. 3,551,556 issued Dec. 29, 1970 to K. Kliment et al., may also be formulated in the form of pellets releasing about the same amounts as shown above and may be implanted subcutaneously or intramuscularly.

Certain peptides of formula 1 which are sparingly soluble in water may be formulated as suspensions either in an aqueous base or in an emulsion base. Aqueous-based suspensions are prepared with the aid of wetting agents for example polyethyleneoxide condensation products of alkyl phenols, fatty alcohols or fatty acids and suspending agents for example hydrophilic colloids such as polyvinylpyrrolidone. Emulsion-based suspensions are prepared by suspending the peptide of formula 1 with the aid of wetting agents and suspending agents in the emulsion base which is prepared with the aid of emulsifying agents such as those described above. The suspension formulations may in addition contain buffering and/or sweetening agents, flavouring agents, colouring materials, preservatives and antioxidants.

As indicated above, the pharmaceutical compositions for oral or parenteral administration of the compounds of formula 1 or of their pharmaceutically acceptable salts are prepared to deliver from 5–100 mcg/kg/day, preferably in divided doses, and may contain from 0.3 to 15 mg of the active ingredient per unit dosage form. For parenteral administration it is preferred to use a water-soluble peptide of formula 1, or a water-soluble salt of a sparingly water-soluble peptide of formula 1, in aqueous sterile solution. Suitable preservatives, for example methyl or propyl p-hydroxybenzoate may be added as well as other solutes, for example sufficient sodium chloride or glucose to make the solution isotonic. Peptides of formula 1 which are sparingly soluble in water may also be administered intramuscularly in solutions or suspensions in sterile liquid carriers other than water, for example suitable vegetable or animal oils, with or without the use of other solutes or of suspending agents as listed above.

PROCESS

The carboxy-terminal amino acid selected to represent C, or B when C is $NHR^1$ as defined above, is protected on the α-amino group, preferably with t-butoxycarbonyl ($R^2$, Boc), and the protected acid is coupled to a hydroxymethyl or preferably to a chloromethylated resin with the aid of a catalyst, preferably cesium bicarbonate or triethylamine. Following the above coupling of the α-amino protected acid the protective group is removed, for example by using trifluoroacetic acid in methylene chloride as described below, or by any one of the other procedures listed above. The deprotection is preferably carried out at a temperature between 0° C. and room temperature.

The preferred chloromethylated resin (1% cross-linked) is commercially available from Bio Rad Laboratories, Richmond, Calif.

The carboxy-terminal amino acid selected to represent C, or B if C is $NHR^1$ as defined above, attached to the resin support by means of the anchoring group Y as defined above is placed in the reaction vessel of an automatic peptide synthesizer programmed to carry out the following wash cycle: (a) methylene chloride; (b) 33% trifluoroacetic in methylene chloride (2 times); (c) methylene chloride; (d) ethanol; (e) chloroform; (f) 10% triethylamine in chloroform (2 times); (g) chloroform; and (h) methylene chloride.

The washed resin is then stirred in methylene chloride with the suitably protected amino acid selected to represent B, or A when C is $NHR^1$ as defined above. The preferred protective group for the α-amino function is t-butoxycarbonyl (Boc); in the amino acids selected to represent B, the preferred protective group for the imidazole nitrogen ($N^{im}$) of histidine is tosyl (Tos); and the preferred protective group for the phenylamino group in p-aminophenylalanine is benzyloxycarbonyl (Z); 3-methylhistidine, β-(pyrazolyl-1)alanine, and β-(2-thienyl)alanine do not require protection except on the α-amino group. A substantially equimolar amount of a coupling reagent, viz, dicyclohexylcarbodiimide or preferably diisopropylcarbodiimide, is added, the mixture is stirred at room temperature (22°–25° C.) for 2 hours and the amino acid resin is then washed successively with methylene chloride (3 times). The attached amino acid is deprotected with 33% trifluoroacetic acid in methylene chloride (2 times) and then steps (c) through (h) as described in the above wash cycle are performed.

The same steps as above are repeated with the suitably protected amino acid selected to represent A when C is an amino acid, and the completed protected peptide resin obtained as described above is washed with methylene chloride (3 times) followed by methanol (3 times) and dried under reduced pressure whereupon substantially all of the theoretical weight gain is obtained (96% or better).

When it is desired to prepare a peptide of formula 1 in which C is $NHR^1$ as defined above, or a peptide of formula 1 in which C is an amino acid lower alkyl amide, the protected peptide resin is suspended in the appropriate lower alkylamine at 0° C. and stirred for several hours. Excess alkylamine is then allowed to evaporate at room temperature and the cleaved peptide is washed from the resin with dimethylformamide. The protected peptide is then precipitated by the addition of ethyl acetate and filtered to give the desired protected peptide in which C is $NHR^1$ as defined above or the respective amino acid lower alkylamide.

When it is desired to obtain the protected peptides in which C is an amino acid amide or an amino acid lower alkyl ester as defined in the first instance the same procedure as above is carried out using ammonia or the respective alcohol plus triethylamine instead of the lower alkylamine.

Removal of protecting groups from the protected peptide, prepared as described above is carried out by treating the material obtained above with hydrogen fluoride and anisole at 0° C. for 15–60 minutes, preferably for about 30 minutes. The hydrogen fluoride is removed under reduced pressure and the anisole removed by washing with ether. When it is desired to obtain the peptides of formula 1 in which C is a free amino acid, the respective protected peptide resin is treated with hydrogen fluoride and anisole as described above. In this manner the protective groups and the attachment to the resin support are both removed at the same time, and the desired peptide of formula 1 in which C is a free amino acid is obtained.

When it is desired to obtain the peptides of formula 1 in which C is 2-aminohydroxyethyl (Gly-ol), the A-B dipeptide resin is treated with 2-aminoethanol to yield the desired peptide of formula 1 in which C is Gly-ol directly; dinitrophenyl or tosyl protective groups, if present on a histidyl residue, are removed at the same time.

BIOLOGICAL TESTING

The appetite and food intake reducing or anorexiant activities of the peptides of formula 1 are determined by means of feeding experiments in mice or in rats substantially in the same manner as described by Trygstad et al, and by Reichelt et al., both cited above. Daily food consumption is measured to 0.1 g, and body weights to 1 g are determined at regular intervals. Other parameters, such as oxygen consumption, body temperature, and plasma glucose and/or insulin levels and quantitative aminograms may also be determined at selected times.

The effects of the peptides of formula 1 upon gastric and/or pancreatic secretion are determined in rats, or preferably in dogs equipped with esophageal, gastric, and pancreatic fistulae as described by Babkin or by Liebling et al., or by Olbe, all cited above. Sham-feeding in dogs resulted in marked increases in the output of acid which reached levels of 82 percent of the maximal acid output obtainable by administering 320 mcg/kg/hour of histamine to the animals (13.55±1.8 mEq/15 mins.); at the same time a significant rise in serum gastrin levels from a basal value of 32±5 pg/ml to 73±10 pg/ml was also observed. Sham-feeding also resulted in a marked increase in pancreatic protein secretion which reached about 71 percent of the maximal levels obtainable by administration of 0.5 mcg/kg/hour of caerulein (650±86 mg/15 mins.). The peptides of formula 1 administered by i.v. infusion at doses of 25-50 mcg/kg/hour thirty minutes before and during sham-feeding reduced the peak output of acid by about 34 percent without significant changes in serum gastrin levels and reduced pancreatic protein secretion by about 38 percent.

In dogs with gastric fistula and Heidenhain pouches the gastric administration of a liver extract meal resulted in a marked increase in acid output which reached about 90% of the maximum obtainable by administration of histamine in dogs with gastric fistula, and about 35 percent of the maximum in dogs with Heidenhain pouches, while serum gastrin levels rose very significantly to more than double of the basal value, from 29±5 pg/ml to 76±12 pg/ml. The peptides of formula 1 administered by i.v. infusion during the plateau of meal induced acid secretion in doses of 50 mcg/kg/hour for one hour reduced those responses to the liver extract meal by 35 percent in dogs with gastric fistula and by 41 percent in dogs with Heidenhain pouches without causing significant changes in serum gastrin levels. Peptides of formula 1 also inhibit the rise in insulin and gastrin in response to feeding.

In dogs with pancreatic fistula ordinary feeding stimulated pancreatic $HCO_3^-$ to 80 percent of the maximal value obtainable by administration of 3 KU/kg/hour of secretin and protein secretion to 92 percent of the maximal value obtainable with 0.5 mcg/kg/hour caerulein. The peptides of formula 1 administered as above during the second hour after feeding reduced $HCO_3^-$ output by 35 percent and protein (enzyme) output by 46 percent without causing retching or other side effects.

The above results indicate clearly that the peptides of formula 1 inhibit the cephalic, the gastric, and the intestinal phases of gastric and pancreatic secretion, probably via suppression of the neuro-hormonal mechanisms responsible for these secretions. Cephalic phase is the neural, psychic or appetite phase of gastric secretion and its inhibition reflects the suppression of appetite and the anorexigenic activity of the peptides of formula 1.

The following non-limitative examples illustrate some selected methods for producing the compounds used in the present invention and procedures for preparing pharmaceutically useful dosage forms thereof.

EXAMPLE 1

D-Pyroglutamyl-L-histidyl
(tosyl)-glycyl—O—CH$_2$-resin,
D-H-(pyro)-Glu-His(N$^{im}$-R$^3$)-Gly—O—CH$_2$-resin,
R$^3$=Tos.

Boc-Glycine resin of the formula:

Boc-Gly—O—CH$_2$-resin (2.70 g, 1.00 mmole of glycine) is placed in the reaction vessel of a Beckman Model 990 automatic peptide synthesizer programmed to carry out the following wash cycle:

(a) methylene chloride; (b) 33% trifluoroacetic acid in methylene chloride (2 times for 1 and 25 minutes each); (c) methylene chloride; (d) ethanol; (e) chloroform; (f) 10% triethylamine in chloroform (2 times for 2 minutes each); (g) chloroform; (h) methylene chloride.

The washed resin is then stirred with t-butyloxycarbonyl-tosylhistidine (3.0 mmoles) in methylene chloride and diisopropylcarbodiimide (3.0 mmoles) is added. The mixture is stirred at room temperature for 1 hour and the peptide resin is subjected to steps (a) through (h) as described in the above wash cycle. D-Pyroglutamic acid (3.0 mmoles) is then coupled by the same cycle of events, to obtain the title compound.

The completed tripeptide resin is washed with methylene chloride (3 times) followed by methanol (3 times) and dried, whereupon 2.89 g of material is obtained.

The glycine resin used in this example is made from a commercially available chloromethylated resin (1% cross-linked, Bio Rad Labs, Richmond, Calif.

EXAMPLE 2

D-Pyroglutamyl-L-histidyl-glycine

The protected tripeptide resin (2.89 g) obtained as described in Example 1 is suspended in hydrogen fluoride (40 ml) and anisole (10 ml) at 0° for 45 minutes. The hydrogen fluoride is evaporated under a stream of dry nitrogen gas and the anisole is removed by washing with ether.

The crude peptide is purified by gel filtration on a column (2.5×95 cm) of Sephadex G 15 (a fine grade, chemically modified, cross-linked dextran), and appropriate fractions (320-340 ml) are lyophilized to yield D-H-(pyro)-Glu-His-Gly-OH as a colourless, fluffy powder (320 mg).

The product is homogeneous by thin layer chromatography in 4 solvent systems on silica gel plates when loads of 20-30 mcg are applied as spots and visualized by exposure to chlorine gas followed by spraying with starch reagent. The following Rf values are obtained: 1-butanol: acetic acid: water (4:1:5, upper phase), 0.08; ethyl acetate: pyridine: acetic acid: water (5:5:1:3), 0.28; 1-butanol: acetic acid: water: ethyl acetate (1:1:1:1), 0.18; 2-propanol: 1 M acetic acid (2:1), 0.20.

Amino acid analysis gives: Glu, 1.03; Gly, 1.00; His, 0.99.

EXAMPLE 3

D-Pyroglutamyl-L-histidyl-glycine (3 parts) is dissolved in distilled pyrogen-free water (1000 parts) and sufficient sodium chloride is added to make the solution isotonic. The mixture is sterilized by autoclaving and filled into vials, to obtain a solution for infusion for therapeutic purposes.

EXAMPLE 4

A mixture of 12 parts of D-pyroglutamyl-L-histidyl-glycine and 500 parts of light magnesium carbonate and 20 parts of magnesium stearate is compressed into slugs. The slugs are broken into granules which are passed through an 8-mesh screen and compressed. There are thus obtained tablets suitable for oral administration for therapeutic purposes.

EXAMPLE 5

A mixture of 12 parts of D-pyroglutamyl-L-histidyl-glycine and 500 parts of light magnesium carbonate is granulated by admixture with a solution of 2 parts of sodium di-octyl sulphosuccinate in a sufficient quantity of methanol. The granules are passed through a 12-mesh screen and dried at 50°-55° C. The granules are then again passed through a 12-mesh screen and 8 parts of magnesium stearate are added and the mixture is compressed. There are thus obtained tablets suitable for oral administration for therapeutic purposes.

EXAMPLE 6

A mixture of 24 parts of D-pyroglutamyl-L-histidyl-glycine, 475 parts of lactose, 94 parts of maize starch and 3 parts of magnesium stearate is compressed into slugs. The slugs are broken into granules which are then passed through an 8-mesh screen. The granules are then coated with a sufficient quantity of a solution of 15 parts of shellac and 3 parts of castor oil in 800 parts of ethyl alcohol; 3 parts of magnesium stearate are then added to the granules after which they are compressed to give tablets suitable for oral use for therapeutic purposes.

EXAMPLE 7

24 parts of D-pyroglutamyl-L-histidyl-glycine are mixed with 576 parts of lactose in a ball-mill and the mixture is filled into gelatine capsules to obtain a dosage form suitable for oral administration for therapeutic purposes.

We claim:

1. A peptide of the formula A-B-C and pharmaceutically acceptable salts thereof in which A is selected from the group consisting of L-pyroglutamyl, D-pyroglutamyl, and L-homo-pyroglutamyl; B is selected from the group consisting of L-histidyl, L-3'-methylhistidyl, D-histidyl, L-phenylalanyl, L-p-aminophenylalanyl, and L-$\beta$-(pyrazolyl-1)alanyl; and C is selected from the group consisting of glycine, glycinamide, glycine (lower alkyl)amides, glycine lower alkyl esters, 2-amino-1-hydroxyethyl, D-alanine, L-$\beta$-(2-thienyl)alanine, and $NHR^1$ in which $R^1$ is lower alkyl, with the proviso that C may not be glycine or glycinamide when A is L-pyroglutamyl and B is L-histidyl.

2. D-Pyroglutamyl-L-histidyl-glycine, as claimed in claim 1.

3. A compound of the formula $R^2$-A-($R^3$-B)-C—O—$CH_2$— resin in which $R^2$ is Boc, $R^3$ is Dnp or Tos, and A, B, and C are defined as follows: A is selected from the group consisting of l-pyroglutamyl, D-pyroglutamyl, and L-homo-pyroglutamyl; B is selected from the group consisting of L-histidyl, L-3'-methylhistidyl, D-histidyl, L-phenylalanyl, L-p-aminophenylalanyl, and L- -(pyrazolyl-1) alanyl; and C is selected from the group consisting of glycine, glycinamide, glycine (lower alkyl) amides, glycine lower alkyl esters, 2-amino-1-hydroxyethyl, D-alanine, L- -(2-thienyl) alanine, and $NHR^1$ in which $R^1$ is lower alkyl, with the proviso that C may not be glycine or glycinamide when A is L-pyroglutamyl and B is L-histidyl.

4. A compound of the formula $R^2$-A-($R^4$-B)-C—O—$CH_2$— resin in which $R^2$ is Boc, $R^4$ is Z, and A, B, and C are as defined in claim 3.

5. t-Butyloxycarbonyl-D-pyroglutamyl-L-($N^{im}$-tosyl)-histidyl-glycyl-O-$CH_2$-resin, as claimed in claim 3.

6. A peptide of the formula A-B-C and pharmaceutically acceptable salts thereof wherein A is selected from the group consisting of L-pyroglutamyl and D-pyroglutamyl; B is selected from the group consisting of L-histidyl when A is D-pyroglutamyl and L-3'-methylhistidyl when A is L-pyroglutamyl; and C is glycine.

* * * * *